United States Patent [19]

Patel et al.

[11] Patent Number: 5,324,662
[45] Date of Patent: Jun. 28, 1994

[54] STEREOSELECTIVE MICROBIAL OR ENZYMATIC REDUCTION OF 3,5-DIOXO ESTERS TO 3-HYDROXY-5-OXO, 3-OXO-5-HYDROXY, AND 3,5-DIHYDROXY ESTERS

[75] Inventors: Ramesh N. Patel, Bridgewater; Clyde G. McNamee, Lawrenceville, both of N.J.; Amit Banerjee, Newtown, Pa.; Laszlo J. Szarka, East Brunswick, N.J.

[73] Assignee: E. R. Squibb & Sons, Inc., Princeton, N.J.

[21] Appl. No.: 883,732

[22] Filed: May 15, 1992

[51] Int. Cl.$^5$ .................. C12P 41/00; C12P 17/10; C12P 7/62
[52] U.S. Cl. .................. 435/280; 435/121; 435/135; 435/822; 435/872; 435/938
[58] Field of Search ............... 435/280, 135, 121, 822, 435/872, 938

[56] References Cited

U.S. PATENT DOCUMENTS

| | | | |
|---|---|---|---|
| 4,584,270 | 4/1986 | Sih | 435/128 |
| 4,601,987 | 7/1986 | Klibanov et al. | 435/280 |
| 4,605,655 | 8/1986 | Yevich et al. | 514/252 |
| 4,607,013 | 8/1986 | Mitsuda et al. | 435/280 |
| 4,800,162 | 1/1989 | Matson | 435/280 |
| 4,897,490 | 6/1990 | Sit et al. | 548/253 |
| 4,994,460 | 2/1991 | Dextraze et al. | 514/252 |
| 5,026,642 | 6/1991 | Radunz et al. | 435/117 |
| 5,084,387 | 1/1992 | Patel et al. | 435/123 |

FOREIGN PATENT DOCUMENTS

| | | |
|---|---|---|
| 080827 | 8/1983 | European Pat. Off. |
| 266217 | 5/1988 | European Pat. Off. |
| 328125 | 8/1989 | European Pat. Off. |
| 350811 | 1/1990 | European Pat. Off. |
| 385172 | 9/1990 | European Pat. Off. |

OTHER PUBLICATIONS

Nieduzak et al., Tetrahedron: Assymetry 2 (1991), 113 to 122.

(List continued on next page.)

Primary Examiner—Douglas W. Robinson
Assistant Examiner—S. Saucier
Attorney, Agent, or Firm—Timothy J. Gaul

[57] ABSTRACT

Microorganisms or reductases derived therefrom reduce a diketo ester

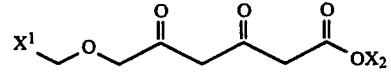

to form the associated 3-hydroxy, 5-hydroxy, or 3,5-dihydroxy esters. Selected microorganisms produce the preferred stereoisomers

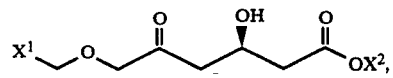

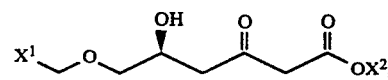

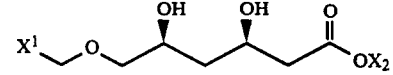

which can be used to prepare antihypercholesterolemic agents such as

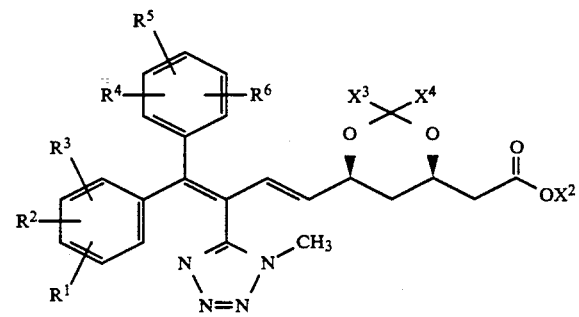

8 Claims, No Drawings

OTHER PUBLICATIONS

Lauman et al., J. Chem. Soc. Chem. Commun. (1988), 598 to 600.
Sih et al., Developments in Industrial Microbiology, vol. 29, (1988), 221 to 229.
Feichter et al., Tetrahedron Letters 30 (5) 1989, 551–552.
Hiratake et al., J. Org. Chem. 53 (26) (1988), 6130–6133.
Bianchi et al., J. Org. Chem. 53 (1988) 5531–5534.
Laumen et al., J. Chem. Soc., Chem. Commun. 3 (1989), 148–150.
Nakamura et al., Agric. Biol. Chem. 54 (6) (1990), 1569–1570.
Cambou et al., J. Am. Chem. Soc. 106 (1984) 2687 to 2692.
Hsu et al., Tet. Lett. 31 (1990), 6403 to 6406.
Babiak et al., J. Org. Chem. 55 (1990), 3377 to 3381.
Sih et al., Angew. Chem. 96 (1984), 556–564.
Hummel W., Appl Microbiol Biotechnol 34:15–19 (1990).
Christen M. et al, J. Chem Soc Chem Commun 264-6 (1988).
Heidlas J. et al, Eur J. Biochem 188:165–174 (1990).
Jones J. B., Tetrahedron 42:3351–3403 (1986).

STEREOSELECTIVE MICROBIAL OR ENZYMATIC REDUCTION OF 3,5-DIOXO ESTERS TO 3-HYDROXY-5-OXO, 3-OXO-5-HYDROXY, AND 3,5-DIHYDROXY ESTERS

FIELD OF THE INVENTION

This invention relates to preparation of chiral intermediates required for chemical synthesis of cholesterol-lowering agents.

BRIEF DESCRIPTION OF THE INVENTION

In accordance with the present invention, a diketo ester

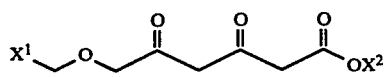

is treated with a reductase-supplying microorganism or a reductase derived therefrom to form an enantiomer of a 3-hydroxy compound

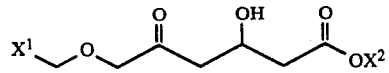

or an enantiomer of a 5-hydroxy compound

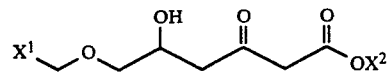

or an enantiomer of a 3,5-dihydroxy compound

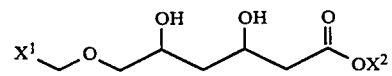

wherein $X^1$ is alkyl, aryl, cycloalkyl, aralkyl, or cycloalkylalkyl and $X^2$ is alkyl. Compounds II and III are further treated with the above reductases or microorganisms to form an enantiomer of compound IV.

Further still in accordance with the present invention, the enantiomer of compound IV reacts with a dialkoxy compound

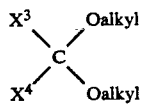

by treatment with an organic acid (e.g., p-toluenesulfonic acid) to form a dioxin

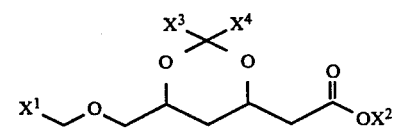

wherein $X^3$ and $X^4$ are each independently hydrogen, alkyl, cycloalkyl, or aryl, or together are alkylene of 4 to 6 carbon atoms, forming a hydrocarbon ring together with the carbon atom to which they are attached. Compound VI is hydrogenated (e.g., with $H_2$ in the presence of palladium on carbon) to form an alcohol

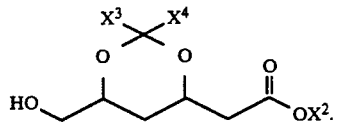

Alcohol VII is oxidized (e.g., Swern oxidation with dimethyl sulfoxide, oxaly chloride, and triethylamine in methylene chloride) to form an aldehyde

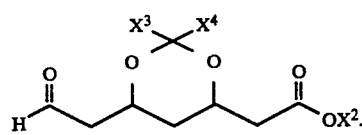

Aldehyde VIII may be used in preparation of cholesterol-lowering agents as described in U.S. Pat. No. 4,897,490, issued Jan. 30, 1990, and the patent applications cited therein. Aldehyde VIII may be coupled with a phospho ester or salt

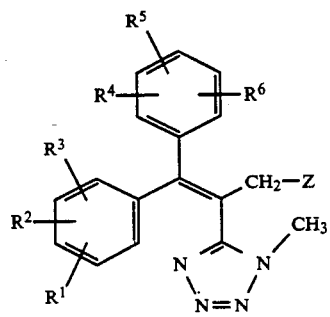

in an inert organic solvent (e.g., tetrahydrofuran or dimethylformamide) in the presence of a strong base (e.g., n-butyllithium) at about $-50°$ to $-78°$ C. to form

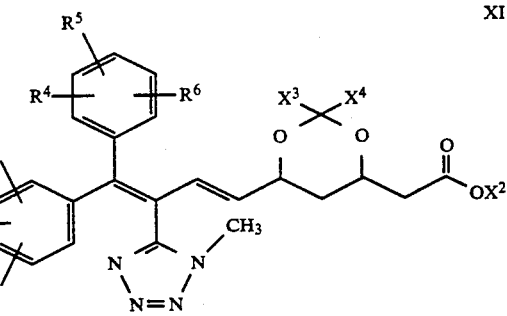

wherein:
  $R^1$ and $R^4$ are each independently hydrogen, halogen, trifluoromethyl, or alkyl or alkoxy of 1 to 4 carbon atoms;
  $R^2$, $R^3$, $R^5$ and $R^6$ are each independently hydrogen, halogen, or alkyl or alkoxy of 1 to 4 carbon atoms;
  Z is

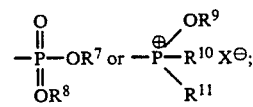

$R^7$ and $R^8$ are each independently alkyl;

$R^9$, $R^{10}$, and $R^{11}$ are each independently phenyl, optionally substituted with one or two substituents selected from chloro and alkyl of 1 to 4 carbon atoms; and X is chloro, bromo, or iodo.

Compound X may be hydrolyzed (e.g., with lithium hydroxide, sodium hydroxide, or potassium hydroxide) to form a salt.

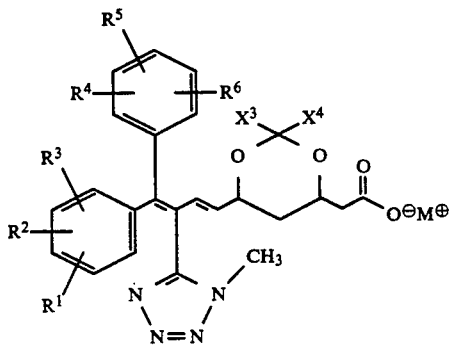

XI wherein M is lithium, sodium or potassium.

DETAILED DESCRIPTION OF THE INVENTION

Definition of Terms

The following definitions apply throughout this specification, unless otherwise limited in specific instances.

The terms "alkyl" and "alkoxy" refer to both straight and branched chain groups. Those groups having 1 to 10 carbon atoms are preferred. The terms "lower alkyl" and "lower alkoxy" refer to groups of 1 to 4 carbon atoms.

The term "cycloalkyl" refers to groups having 3, 4, 5, 6 or 7 carbon atoms.

The term "aryl" refers to phenyl and substituted phenyl. Exemplary substituted phenyl groups are substituted with 1, 2 or 3 amino (-NH₂), alkylamino, dialkylamino, nitro, halogen, hydroxyl, trifluoromethyl, lower alkyl, lower alkoxy, alkanoyloxy, carbamoyl, carboxyl, or carboxy (lower alkyl) groups.

The term "alkanoyl" refers to groups of the formula -C(O)alkyl having 1 to 5 carbon atoms.

The term "halogen" refers to fluorine, chlorine, bromine and iodine.

Process of Preparation

The process of this invention can be carried out in a single stage or a two-stage fermentation and transformation process.

In the single stage process, the microorganisms are grown in an appropriate medium containing carbon and nitrogen sources. After sufficient growth of microorganisms, a compound of formula I is added to the microbial cultures and the transformation may be continued until complete conversion is obtained.

In the two-stage process, microorganisms are grown in an appropriate medium by fermentation exhibiting the desired oxide-reductase activity in the first stage. Subsequently, cells are harvested by centrifugation. Microbial cell suspensions are prepared by suspending harvested cells in an appropriate buffered solution. Buffers such as tris-HCl, phosphates, sodium acetate and the like may be used. Water can also be used to prepare suspensions of microbial cells to conduct the transformation process.

Compound I is mixed with the microbial cell suspensions, and the transformation of compound I is catalyzed by the microbial cell suspensions. The reaction may continue until nearly all of compound I is transformed.

Microorganisms can be used in free state as wet cells, freeze-dried cells or heat-dried cells. Immobilized cells on support by physical adsorption or entrapment can also be used for this process. Microbially derived oxidoreductases may be used in free state or immobilized on support.

Appropriate media for growing microorganisms are those which provide nutrients necessary for the growth of the microbial cells. A typical medium for growth includes necessary carbon sources, nitrogen sources, and trace elements. Inducers may also be added. "Inducer" as used herein means any compounds containing keto groups such that the desired oxido-reductase enzyme is produced within the microbial cell. Formula I compounds can be added as inducers during growth of the microorganism.

Carbon sources include sugars such as maltose, lactose, glucose, fructose, glycerol, sorbitol, sucrose, starch, mannitol, propylene glycol, and the like; organic acids such as sodium acetate, sodium citrate, and the like; amino acids such as sodium glutamate and the like; alcohols such as ethanol, propanol, and the like.

Nitrogen sources include N-Z amine A, corn steep liquor, soy bean meal, beef extracts, yeast extracts, molasses, baker's yeast, tryptone, nutrisoy, peptone, yeastamin, sodium nitrate, ammonium sulfate, and the like.

Trace elements included phosphates and magnesium, manganese, calcium, cobalt, nickel, iron, sodium, and potassium salts.

It is within the scope of this invention that appropriate media may include more than one carbon or nitrogen source and may include a mixture of several.

| Medium 1 | |
|---|---|
| Malt Extract | 1% |
| Yeast Extract | 1% |
| Peptone | 1% |
| Glucose | 2% |
| | pH 7.0. |
| Medium 2 | |
| Peptone | 0.3% |
| Glycerel | 4% |
| Malt Extract | 1% |
| Yeast Extract | 1% |
| | pH 7.0. |
| Medium 3 | |
| Peptone | 0.3% |
| Fructose | 2% |
| Malt Extract | 1% |
| Yeast Extract | 1% |
| | pH 7.0. |
| Medium 4 | |
| Sodium Succinate | 2% |
| Malt extract | 1% |
| Yeast extract | 1% |
| Peptone | 0.3% |
| | pH 7.0. |

The pH of the medium should be adjusted to about 6 to 8, preferably 6.5, before sterilization at 121° C. for 30 minutes and to about 6.5 to 7.5, preferably 7.0, after sterilization.

The pH of the medium may be maintained between 4.0 and 9.0, preferably between 6.0 and 8.0, during growth of microorganisms and during the transformation process.

The temperature of the reaction mixture should be maintained to ensure that there is sufficient energy available for the process. The temperature is a measure of the heat energy available for the transformation process. A suitable temperature range is from about 15° C. to 60° C. A preferred temperature range is from about 25° C. to 40° C.

The agitation and aeration of the reaction mixture affects the amount of oxygen available during the transformation process in shake-flask cultures or fermenter tanks during growth of microorganisms in a single stage or two-stage process. The agitation range from 50 to 1000 RPM is preferable, but 50 to 500 RPM is most preferred. Aeration of about 0.1 to 5 volumes of air per volume of media per minute (i.e., 0.1 to 10 v/vt) is preferred. Aeration of about 5 volumes of air per volume of media per minute (i.e., 5 v/vt) is most preferred.

Complete conversion of compound I takes about 12 to 48 hours, preferably 4 to 24 hours, measured from the time of initially treating compound I with the microorganism or enzyme.

The transformation may be carried out using nicotinamide adenine dinucleotide (NADH) as a co-factor. NADH may thereafter be regenerated and reused as in Example 3 hereinafter.

Typical microorganisms for this process include genera from bacteria, yeasts, and fungi. Typical genera of microorganisms include: Achromobacter, Acinetobacter, Actinomyces, Alkaligenes, Arthrobacter, Azotobacter, Bacillus, Brevibacterium, Corynebacterium, Flavobacterium, Methylomonas, Mycobacterium, Nocardia, Pseudomonas, Rhodococcus, Streptomyces, Xanthomonas, Aspergillus, Candida, Fusarium, Geotrichum, Hansenula, Kloeckera, Penicillium, Pichia, Rhizopus, Rhodotorula, Saccharomyces, Trichoderma, Mortierella, Cunninghamella, Torulopsis, and Rhodopseudomonas. Preferred microorganisms include *Arthrobacter simplex, Nocardia globerula, Nocardia restricta, Nocardia salmonicolor, Rhodococcus fascians, Rhodococcus rhodochrous, Mycobacterium vacca, Nocardia meditteranei, Nocardia autotrophica, Rhodococcus equi, Hansenula polymorpha, Candida albicans, Geotrichum candidum*, and *Saccharomyces cerevisiae, Mortierella alpina, Pichia pastoris, Pichia methanolica, Hansenula polymorpha, Cunninghamella echinalate, Saccharamyces cerevisiae, Geotrichum candidum, Mortierella alpina, Nocardia globerula, Torulopsis polysporium*, and *Acinetobacter calcoaceticus*. Most preferred microorganisms include *Pichia methanolica, Pichia pastoris, Geotrichum candidum, Torulopsis glabrata, Mortierella alpina, Nocardia globerula*, and *Acinetobacter calcoaceticus*.

The transformation of compound I may also be accomplished by reductase isolated from microorganisms. The isolation may be accomplished by homogenizing cell suspensions, followed by disintegration, centrifugation, DEAE-cellulose chromatography, Ammonium sulfate fractionation, Sephacryl chromatography, and Mono-Q chromatography. Further detail on isolation procedures is described in Example 5.

For each of the processes of the present invention, $X^1$ is preferred to be phenyl and $X^2$ is preferred to be ethyl. $X^3$ and $X^4$ are preferred to be methyl. Compounds II, III and IV are preferred to have the following stereochemistry:

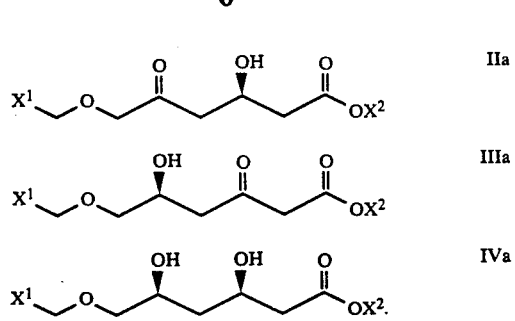

The stereochemistry of compound IVa will then carry through compounds V–VIII and X. Compound IX is preferred to be

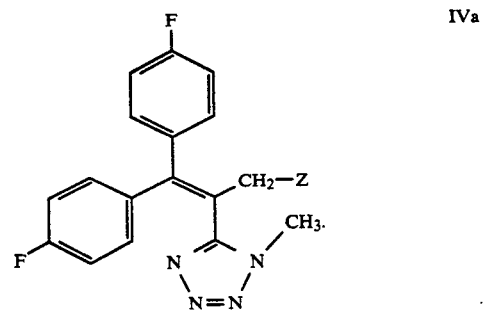

The preferred final product compound X is

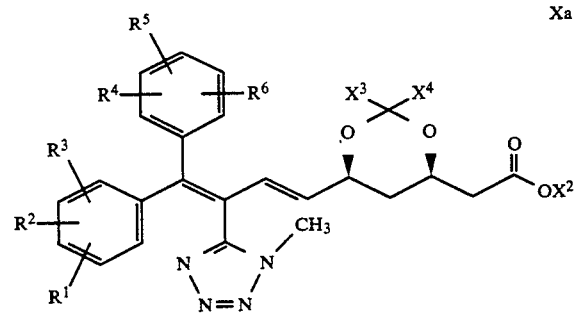

and the most preferred is

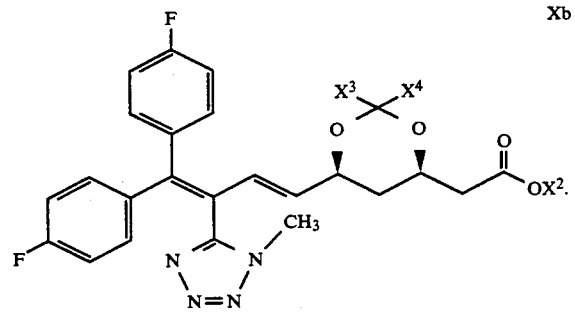

For preparation of the preferred stereoisomers IIa through Xa, compound I is preferably treated with *Pichia methanolica, Pichia pastoris, Geotrichum candidum, Nocardia globerula, Acinetobacter calcoaceticus*, or a reductase derived from any of these. *Acinetobacter calcoaceticus* is the most preferred species. Preferred strains are listed in Table 1 of Example 1.

The following working examples describe the manner and process of making and using the invention. These examples are preferred embodiments and are illustrative rather than limiting. It should be understood that there may be other embodiments which fall within the spirit and scope of the invention as defined by the claims appended hereto.

EXAMPLE 1

Use of whole cells: various strains

The substrate for this process (compound A) is the compound having the formula

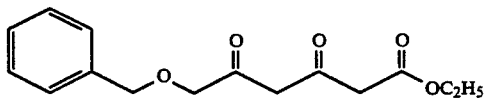   A and the name 3,5-dioxo-6-(benzyloxy)hexanoic acid, ethyl ester. The desired product (compound B) is the compound having the formula

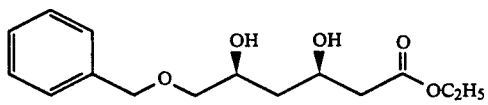   B and the name (R,S)-3,5-dihydroxy-6-(benzyloxy)hexanoic acid, ethyl ester.

Other products are compound C, having the formula

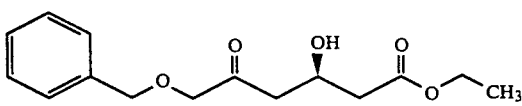   C and the name R-3-hydroxy-5-oxo-6-(benzyloxy)hexanoic acid, ethyl ester, and compound D, having the formula

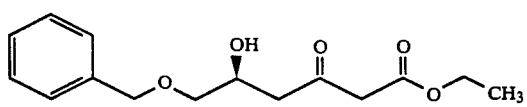   D and the name S-5-hydroxy-3-oxo-6-(benzyloxy)hexanoic acid, ethyl ester.

The microorganisms were maintained in a vial in liquid nitrogen. For routine development of inoculum, one vial was inoculated into 100 mL of medium 1 in a 500-mL flask and incubated at 28° C. and 280 RPM on a shaker for 48 hours. After growth of the microorganism, 10 mL of culture was inoculated into a 500-mL flask containing 100 mL of medium 1 and incubated at 28° C. and 250 RPM on a shaker.

Cells were harvested and suspended in 10 mM potassium phosphate buffer pH 6.8. 10 mL of 20% w/v cell-suspensions were prepared. Cell-suspensions were supplemented with 25 mg of substrate (compound A) and 750 mg of glucose and the transformations were conducted at 28° C., 150 RPM for 48 hours. One volume of sample was taken and extracted with two volumes of 65:35 hexane:n-butanol, and the separated organic phase was filtered through a 0.2 μm LID/x filter and collected.

Samples (in 65:35, hexane:n-butanol mixture) were analyzed for substrate and product concentration by Hewlett Packard 1070 HPLC System. A HP-hypersil ODS (5 μm) column (200×4.6 mm) was used. The mobile phase consisted of 50% water and 50% acetonitrile mixture. The flow rate was 1 mL/min at ambient temperature. The detection wavelength was 220 nm. The retention times for compounds A and B were 6.74 and 3.17 minutes, respectively.

The separation of compounds C and D was achieved by HPLC. Two columns C18 (polyspher RP-18, 150×0.4 mm and Chiralcel OD, 250×0.4 mm) in series were used. Column 1 was maintained at about 25° C. and column 2 at about 0° C. The mobile phase consisted of methanol: n-butanol:hexane (5:1:94) was used at a flow rate of 0.8 mL/mm. The detection wavelength was 220 nm. The reaction times for compound C and compound D were 9.4 and 11.3 minutes, respectively.

Compounds C and D were then each separated from their respective undesired enantiomers on a Chiracel OD column. The mobile phase consisted of methanol:1-propanol:hexane (2:1:97) with 0.01 mol beta-cyclodextrin. The flow rate was 0.5 mL/minute and the detection wavelength was 220 nm. The retention times for compounds C and D were 19.1 and 23.5 minutes, respectively.

The separation of the two enantiomers of the racemate of the product B was achieved on a Chiracel OB column. The mobile phase consisted of 63.5:31.5:5 of hexane: n-butanol:isopropanol. The flow rate was 1 mL/mm and the detection wavelength was 230 nm. The retention times for the desired enantiomer (compound B) was 14.2 minutes and the undesired enantiomer was 19.8 minutes.

Experimental results obtained by using various microorganisms grown on medium 1 and following the procedure of Example 1 are shown in Table 1.

Some organisms stereoselectively reduced compound A to the desired compound B and some organisms converted compound A to compound E having the formula

TABLE 1

| Microorganisms | Reaction Yield | Compound B | Compound E |
|---|---|---|---|
| Pichia methanolica ATCC 58403 | 56 | 89 | — |
| Hansenula polymorpha ATCC 26012 | 52 | — | 90 |
| Pichia pastoris ATCC 28485 | 48 | 92 | — |
| Cunninghamella echinalate ATCC 9244 | 15 | — | 89 |
| Saccharomyces cerevisiae ATCC 12341 | 18 | — | 75 |
| Geotrichum candidum ATCC 34614 | 40 | 78 | — |
| Mortierella alpina ATCC 16266 | 78 | — | 85 |
| Nocardia globerula ATCC 21505 | 48 | 91 | — |
| Acinetobacter calcoaceticus ATCC 33305 | 85 | 97 | — |

EXAMPLE 2

Use of whole cells: time study

The substrate for this process is (compound A) and the desired product (compound B) are as described in Example 1.

Cells of *Acinetobacter calcoaceticus* ATCC 33305 were grown in 100 mL of medium 1 combined in a 500-mL flanks. Growth was carried out at 25° C. for 48 hours at 280 RPM. 100 mL of cultures were inoculated into 15 L of medium 2 combined in a fermentor. Growth in a fermentor was carried out at 25° C., 15 LPM aeration and 500 RPM agitation for 30 hours. Cells were harvested from the fermentor and used for the biotransformation of compound A to compound B.

Cells (300 grams) were suspended in 3 liters of 10 mM potassium phosphate buffer, pH 6.0, and homogenous cell suspensions were prepared. 6 grams of compound A and 75 grams of glucose were added to the cell suspensions and the biotransformation of compound A to compound B was carried out at 28° C., 160 RPM for 24 hours. Results are summarized in Table 2. Samples were prepared and product yield and optical purity were determined as described in Example 1.

TABLE 2

| Reaction Time (Hours) | Compound B g/L | Yield (%) | Optical Purity % |
|---|---|---|---|
| 4  | 0.68 | 38 | — |
| 20 | 1.54 | 87 | — |
| 23 | 1.66 | 86 | 99% |

EXAMPLE 3

Use of cell extracts and co-factor

The substrate for this process (compound A) and the desired product (compound B) are described in Example 1.

Cells of *Acinetobacter calcoaceticus* ATCC 33305 were grown on medium 1 and medium 2 as described in Example 2.

Cells (150 grams) were suspended in 1.5 L of 0.2M potassium phosphate buffer, pH 6.0. The homogenized cell suspensions were disintegrated as 4° C. by Microfluidizer at 13,000 psi pressure. The disintegrated cell suspension was centrifuged at 12,000 RPM for 30 minutes. The clear supernatant ("cell extracts") was used for the biotransformation of compound A to compound B.

One liter of cell extract was supplemented with 10 grams of substrate (compound A), glucose dehydrogenase (3500 units), 0.7 mM NAD+ (nicotinamide adenine dinucleotide), and 100 grams of glucose. The reaction was carried out in a pH stat at pH 6.0, 150 RPM agitation, and 30° C. Periodically, samples were taken and analyzed for the reaction yield and optical purity of compound B as described in Example 1. Results are as shown in Table 3.

TABLE 3

| Reaction Time (Hours) | Compound B g/L | Yield (%) | Optical Purity % |
|---|---|---|---|
| 24 | 8.2 | 82 | >99% |

In the above experiment, the NADH cofactor used for the biotransformation of compound A to compound B was regenerated using glucose dehydrogenase, NAD+, and glucose as shown below.

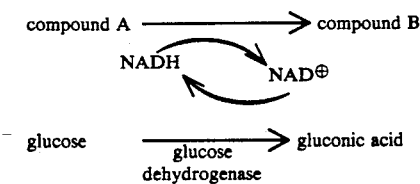

After complete conversion of compound A to compound B, the reaction mixture is adjusted to pH 7.0 and extracted three times with equal volumes of dichloromethane. The organic phase was separated and washed twice with 0.7M sodium bicarbonate. The separated organic layer was dried over anhydrous sodium sulfate and dichloromethane was removed under reduced pressure. The resulting oily residue was dried under vacuum at room temperature to recover a pale yellow solid in 85% yield and 99% optical purity.

EXAMPLE 4

Use of cell extracts: time study

The substrate and desired products are as described in Example 1.

Growth of *Acinetobacter calcoaceticus* ATCC 33305 was carried out on medium 1 and medium 2 as described in Example 2. The preparation of cell extracts and the biotransformation of compound A to compounds B, C and D with cell extracts were carried out as described in Example 3. The reaction was terminated after 16 hours. Results are as shown in Table 4. Product concentrations were analyzed by HPLC as described in Example 1. The cofactor NADH was regenerated as described in Example 3.

TABLE 4

| Reaction Time (Hours) | Compound B g/L | Compound C and D Mixture G/L |
|---|---|---|
| 16 | 2.61 | 4.8 |

Compounds C and D were isolated by the following procedure.

Centrifuged cell extracts (1 L, 4.8 g of compounds C and D)
↓
pH adjusted to 7.0;
extracted three times with equal volumes of dichloromethane;
organic layer separated (centrifugation required to break up emulsion);
organic layer washed twice with 7% sodium chloride,
organic layer dried over anhydrous sodium sulfate,
dichloromethane removed under reduced pressure.
↓
Viscous, oily liquid (4.8 g)
↓
dried under vacuum at room temperature;
↓
Dark Brown Liquid (2.1 g of compounds C and D)
↓
loaded on neutralized silica column (35 × 2.0 cm);
washed with 80:20, 70:30, and 60:40 hexane: ethyl acetate (100 mL each);
Fraction #34–39 collected (2 mL fractions);
Solvent removed under reduced pressure;
↓
Pale Yellow Liquid, 0.6 g of compound C and D mixture HPLC HI 90%.

Compounds C and D were then separated by preparative HPLC as decribed in Example 1.

EXAMPLE 5

Use of purified reductase

The substrate for this process (compound A) and the desired product (compound B) are described in Example 1.

Growth of *Acinetobacter calcoaceticus* ATCC 33305 was carried out on medium 1 as described in Example 2. Cell extracts of *Acinetobacter calcoaceticus* ATCC 33305 were prepared as described in Example 3.

Cell extracts (700 mL) were loaded onto a DEAE-cellulose (DE-52) column and eluted with buffer containing sodium chloride in a linear gradient from 0–0.5M. Fractions containing reductase activity were pooled and concentrated by ammonium sulfate precipitation (70% saturation). Precipitated material was collected by centrifugation, dissolved in buffer, and loaded onto Sephacryl S-200 column. Fractions containing reductase activity were pooled after chromatography and loaded onto a Mono-Q column. Proteins bound on the Mono-Q column were eluted with a buffer containing sodium chloride in a linear gradient from 0 to 0.5M. Fractions having reductase activity were pooled and analyzed by sodium dodecyl sulfate (SDS) gel electrophoresis. The purified enzyme was homogeneous, with a molecular weight of 35,000±3,000 daltons. The specific activities during purification procedures are as shown in Table 5.

TABLE 5

| Steps | Volume (mL) | Total Activity μmol/min | Total Protein (mg) | Specific Activity μmol/min/ mg protein | Purification (fold) |
|---|---|---|---|---|---|
| 1. Cell extracts | 700 | 147.2 | 4480 | 0.033 | — |
| 2. DEAE-cellulose column chromatography | 700 | 141.6 | 1120 | 0.126 | 3.8 |
| 3. Ammonium sulfate fractionation (0–70%) | 30 | 134.4 | 568.8 | 0.23 | 6.95 |
| 4. Sephacryl S-200 column chromatography | 15 | 19.2 | 4.04 | 4.75 | 144 |
| 5. Mono-Q column | 20 | 3.92 | 0.536 | 7.31 | 222 |

The transformation of compound A to compound B was carried out by the purified enzyme (Mono-Q fraction). The reaction mixture in 20 mL of 0.1M potassium phosphate buffer (pH 6.0) contained 10 unit of purified reductase enzyme, 200 mg of substrate (compound A), 100 units of glucose dehydrogenase, 1 gram of glucose, and 50 mg of NAD+. The reaction was carried out in a pH stat at pH 6.0, 100 RPM agitation and 25° C. for 16 hours. Product (compound B) and substrate (compound A) concentrations were estimated by the procedures described in Example 1. After 16 hours of reaction time, an 89% reaction yield and greater than 99% optical purity of compound B was obtained.

What is claimed is:

1. A process comprising:
   (a) treating a diketo ester of the formula

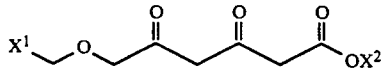

with a microorganism selected from *Pichia methanolica, Pichia pastoris, Geotrichum candidum, Nocardia globerula* and *Acinetobacter calcoaceticus* or a reductase derived from any of these microorganisms to form a 3,5-dihydroxy enantiomer of the formula

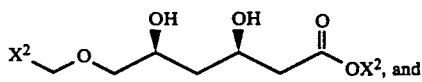

(b) recovering the 3,5-dihydroxy enantiomer therefrom; wherein $X^1$ is alkyl, aryl, cycloalkyl, aralkyl, or cycloalkylalkyl and $X^2$ is alkyl.

2. The process of claim 1, wherein $X^1$ is phenyl and $X^2$ is ethyl.

3. A process comprising:
   (a) treating a diketo ester of the formula

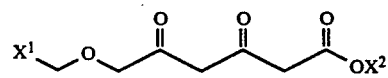

wherein $X^1$ is alkyl, aryl, cycloalkyl, aralkyl, or cycloalkylalkyl and $X^2$ is alkyl, with a microorganism selected from the group consisting of *Pichia methanolica, Pichia pastoris, Nocardia globerula* and *Acinetobacter calcoaceticus* or a reductase derived from any of these microorganisms to form a 3,5-dihydroxy enantiomer of the formula

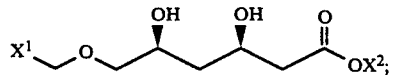

(b) recovering the 3,5-dihydroxy enantiomer therefrom;
   (c) coupling the 3,5-dihydroxy enantiomer with a dialkoxy compound of the formula

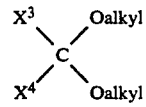

wherein $X^3$ and $X^4$ are each independently hydrogen, alkyl, cycloalkyl, or aryl, or together are alkylene of 4 to 6 carbon atoms, forming a hydrocarbon ring together with the carbon atom to which they are attached, to form a dioxin ether of the formula (d) hydrogenating the dioxin ether to form an alcohol of the formula

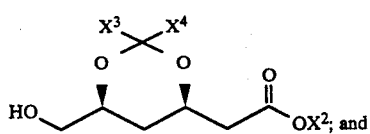

(e) oxidizing the alcohol to form an aldehyde of the formula

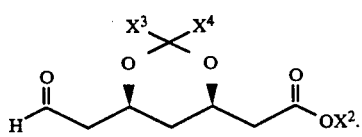

4. The process of claim 3, further comprising reacting the aldehyde product of claim 3 having the formula

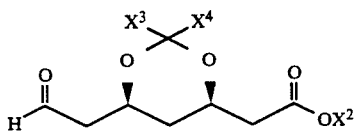

with a compound of the formula

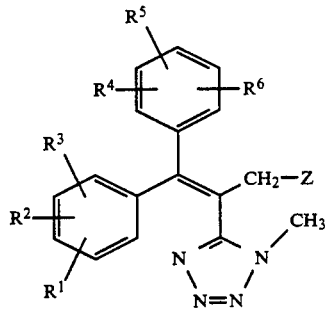

to form a product of the formula

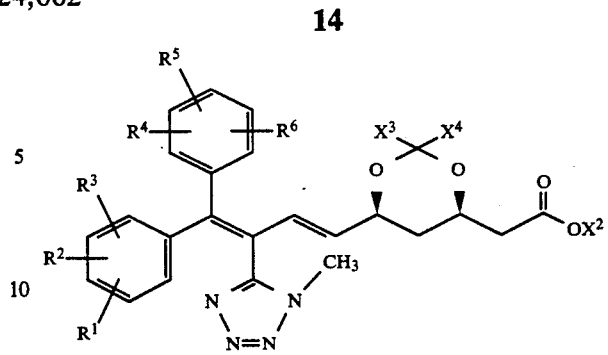

wherein:
$X^3$ and $X^4$ are each independently hydrogen, alkyl, cycloalkyl, or aryl, or together are alkylene of 4 to 6 carbon atoms, forming a hydrocarbon ring together with the carbon atom to which they are attached;
$R^1$ and $R^4$ are each independently hydrogen, halogen, trifluoromethyl, or alkyl or alkoxy of 1 to 4 carbon atoms;
$R^2$, $R^3$, $R^5$ and $R^6$ are each independently hydrogen, halogen, or alkyl or alkoxy of 1 to 4 carbon atoms;
Z is

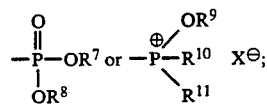

$R^7$ and $R^8$ are each independently alkyl; and
$R^9$, $R^{10}$, and $R^{11}$ are each independently phenyl, optionally substituted with one or two substituents selected from chloro and alkyl of 1 to 4 carbon atoms.

5. The process of claim 3, wherein $X^1$ is phenyl and $X^2$ is ethyl.

6. The process of claim 3, wherein $X^3$ and $X^4$ are methyl.

7. The process of claim 4, wherein:
one of $R^1$, $R^2$ and $R^3$ is para-fluoro and the other two are hydrogen; and
one of $R^4$, $R^5$ and $R^6$ is para-fluoro an the other two are hydrogen.

8. The process of claim 4, wherein:
$X^1$ is phenyl and $X^2$ is ethyl;
$X^3$ and $X^4$ are methyl;
one of $R^1$, $R^2$ and $R^3$ is para-fluoro and the other two are hydrogen; and
one of $R^4$, $R^5$ and $R^6$ is para-fluoro and the other two are hydrogen.

* * * * *